United States Patent
Santi et al.

(10) Patent No.: US 6,459,007 B1
(45) Date of Patent: Oct. 1, 2002

(54) PROCESS FOR THE PREPARATION OF 1-HEXENE

(75) Inventors: Roberto Santi; Anna Maria Romano, both of Novara; Manuela Grande, Vercelli; Anna Sommazzi, Genoa; Francesco Masi, Lodi; Antonio Proto, Novara, all of (IT)

(73) Assignee: Enichem S.p.A., San Donato Milanese (IT)

( * ) Notice: Subject to any disclaimer, the term of this patent is extended or adjusted under 35 U.S.C. 154(b) by 0 days.

(21) Appl. No.: 09/926,555
(22) PCT Filed: Mar. 12, 2001
(86) PCT No.: PCT/EP01/02827
§ 371 (c)(1),
(2), (4) Date: Feb. 11, 2002
(87) PCT Pub. No.: WO01/68572
PCT Pub. Date: Sep. 20, 2001

(30) Foreign Application Priority Data

Mar. 17, 2000 (IT) .......................................... MI00A0546

(51) Int. Cl.$^7$ .............................. C07C 2/34; C07C 2/26
(52) U.S. Cl. .................... 585/511; 585/512; 585/515
(58) Field of Search .................................. 585/511, 512, 585/515

(56) References Cited

FOREIGN PATENT DOCUMENTS

DE     44 36 113     4/1996

*Primary Examiner*—Thuan D. Dang
(74) *Attorney, Agent, or Firm*—Oblon, Spivak, McClelland, Maier & Neustadt, P.C.

(57) ABSTRACT

Process for the preparation of 1-hexane consisting in effecting the oligomerization of ethylene in the presence of a catalyst comprising a vanaduim complex having the formula: (arene)$_2$ VX wherein the term arene represents benzene or mono-, di-, or tri-alkylsubstituted benzene, V is a vanaduim ion with a low wxidation state, and X is an anion selected from non-coordinated anions such as B(Ar)$_4$—, AlCl$_4$—, carboxylates and sulfonates.

14 Claims, No Drawings

PROCESS FOR THE PREPARATION OF 1-HEXENE

The present invention relates to a process for the preparation of 1-hexene by the oligomerization of ethylene in the presence of vanadium complexes with a low oxidation state.

The possibility of preparing olefins with a double terminal bond by means of the oligomerization of lower olefins, for example 1-hexene by the trimerization of ethylene, is already known: for example U.S. Pat. No. 4,668,838 describes a process involving the use of a catalyst which comprises the reaction product between a chromium compound, a hydrocarbon derivative of partially hydrolyzed aluminum and a ligand-donor compound; European patent application Ser. No. 416,304 involves, in the process in question, the use of a catalytic system comprising a pyrrolidic compound of chromium and a compound of aluminum; European patent application 537,609 relates to the process of interest which is carried out in the presence of a catalyst consisting of a complex of chromium with a polydentate ligand and an aluminoxane.

In addition to the above references, others can be cited relating to the use of catalytic systems based on compounds of chromium; preparation processes of 1-hexene by the oligomerization of ethylene in the presence of these catalytic systems, however, seem to have various drawbacks such as, for example, insufficient activity of the catalyst or difficulty in its preparation or the low selectivity with respect to the desired product.

The Applicant has now found that it is possible to effect the synthesis of 1-hexene by the oligomerization of ethylene using a process which overcomes all the disadvantages which negatively characterize analogous processes described in the state of the art above, and which consequently seem to have all the necessary industrial requisites. The object of the invention, according to the present patent application, therefore relates to a process for the preparation of 1-hexene which consists in subjecting ethylene to oligomerization in the presence of a catalyst comprising a vanadium complex with a low oxidation state selected from those included in the follow formula:

(arene)$_2$VX wherein the term arene represents benzene or mono-, di-, or tri-alkylsubstituted benzene, V is a vanadium ion with a low oxidation state, and X is an anion selected from non-coordinating anions such as B(Ar)$_4^-$, AlCl$_4^-$, carboxylates and sulfonates.

The following complexes have proven to be particularly advantageous:

bis-(mesitylene)-vanadium trifluoroacetate
bis-(mesitylene)-vanadium-tetraphenylborate
bis-(mesitylene)-vanadium-tetrachloroaluminate.

Vanadium arenes are already known in the art and can be prepared for example according to the indications, which form an integral part of the present invention, contained in the articles of E. O. Fischer and U. S. Kogler, Chem. Ber. 90, 250 (1957), and F. Calderazzo, Inorg. Chem., 3, 810 (1964): for example according to the schemes of Table 1.

In accordance with a wider aspect of the process of the present invention, these vanadium complexes can be used for the oligomerization of olefins other than ethylene, such as, for example, propylene, 1-butene, etc.: the reason the Applicant has decided to limit the description of the invention to the preparation of 1-hexene alone is simply because of the specific industrial interest in the production of this compound: any expert in the field will be able to understand from this description how to effect the oligomerization reaction starting from olefins other than ethylene, this process being included, however, in the scope of the invention according to the present patent application.

The oligomerization reaction of ethylene, according to the process of the present invention is carried out in the absence of co-catalysts, in the presence of the above vanadium compound alone or in the presence of the vanadium compound and a heterocyclic compound selected from pyrrole and derivatives.

When this heterocyclic compound is adopted, it is used in a ratio, with respect to the vanadium complex, ranging from 1 to 20: heterocyclic compounds which can be advantageously used are pyrroles, pyrazoles, phenanthroline, pyridine and other mono and polynitrogenated derivatives.

The oligomerization reaction of ethylene, according to the present invention, is carried out in the presence of a solvent which is normally selected from aromatic hydrocarbons and cycloaliphatic hydrocarbons: of these, the use of toluene and cyclohexane has proved to be particularly advantageous.

The reaction is carried out at a temperature ranging from 0 to 150° C., preferably from 25 to 60° C., and at a pressure ranging from 1 to 100 atm., preferably from 1 to 50 atmospheres. The reaction time is normally less than 36 hours, preferably from 1 to 24 hours. At the end of the reaction, 1-hexene can be separated and recovered from the reaction mixture using techniques well known to experts in the field.

Further details are evident from the following operative examples which are provided for a better illustration of the present invention without limiting its scope however in any way.

TABLE I

VANADIUM COMPLEXES

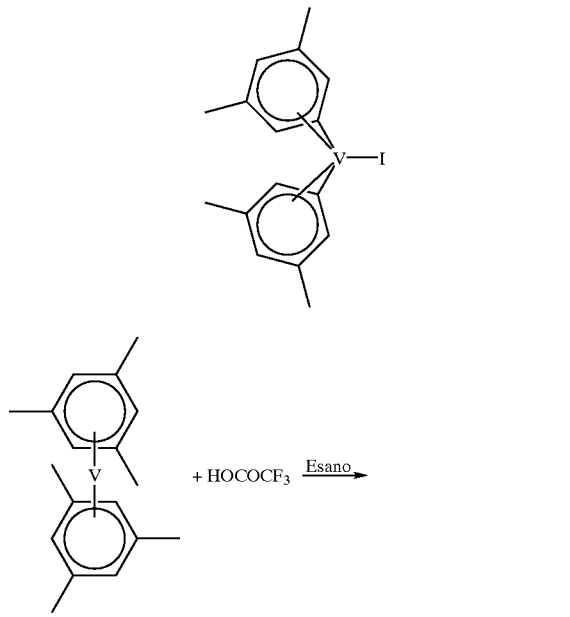

TABLE I-continued

VANADIUM COMPLEXES

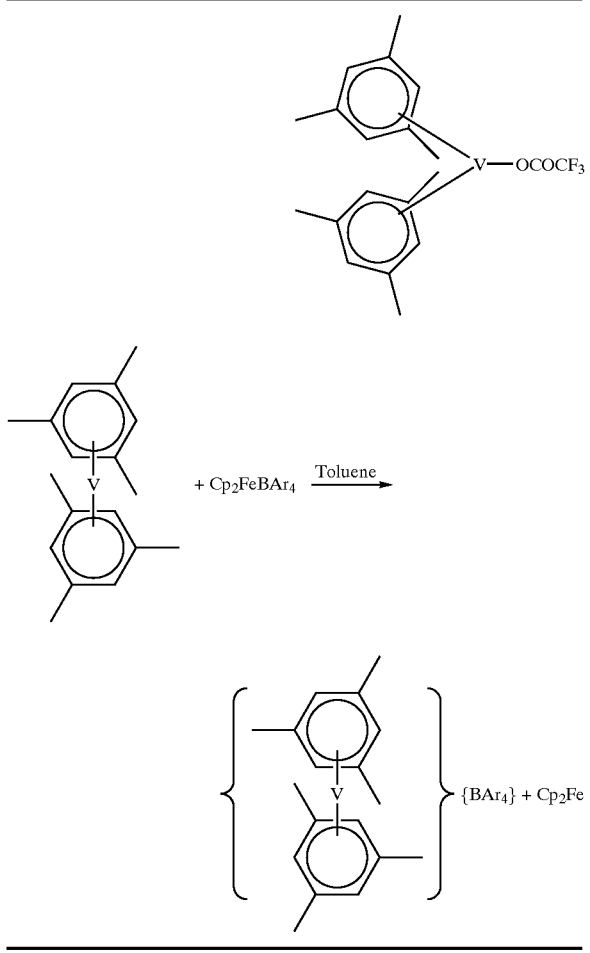

Ar = Ph, C$_6$H$_5$.

EXAMPLE 1

Synthesis of V(mes)$_2$(OCOCF$_3$)

1.723 g of V(mes)$_2$ (5.9 mmoles) and 50 ml of anhydrous and degassed n-hexane are charged under argon into a 250 ml test-tube. 0.44 ml of anhydrified trifluoroacetic acid CF$_3$COOH (5.9 mmoles) are added to the brown solution. A brown precipitate is formed which, after 4 hours, is filtered and washed with hexane 6 times. The brown, pump-dried solid weighs 1.2 g (yield 52%).

EXAMPLE 2

Synthesis of ferrocene tetraphenyl borate Cp$_2$Fe (BPh$_4$)

1.13 g of ferrocene Cp$_2$Fe (MW=186; 6.10 mmoles) are charged into a 100 ml flask and 10 ml of H$_2$SO$_4$ at 96% are slowly added dropwise. There is a substantial development of heat. 2.6 g of Na(BPh$_4$) (MW=342; 7.63 mmoles) dissolved in 25 ml of water are slowly added dropwise to the blue solution, Cp$_2$Fe(HSO$_4$). A blue precipitate is formed, which is filtered and washed with ethanol (5×10 ml), followed by ethyl ether (5×10 ml) and finally dried for a whole night with a vacuum pump and subsequently on P$_2$O$_5$.

EXAMPLE 3

Synthesis of Vanadium bis-(mesitylene)tetra phenyl borate V(mes)$_2$(BPh$_4$)

0.350 g of Cp$_2$Fe(BPh$_4$) (MW=505; 0.7 mmoles) and 0.201 g of V(mes)$_2$ (MW=291; 0.7 mmoles) are charged under argon into a 100 ml test-tube containing 30 ml of anhydrous toluene. The mixture is left under stirring for about 4 hours; the dark solid product is filtered and dried. 0.410 g of product are obtained (yield: 96%).

EXAMPLE 4

36 mg of V(mes)$_2$(OCOCF3) (MW=404; 0.089 mmoles) are charged under argon into a 100 ml three-necked flask. 20 ml of anhydrous and degassed toluene are added. The resulting brown solution under ethylene becomes lighter. It is left at 45° C. for 24 hours. The absorption buret registers an ethylene consumption equal to 500 ml. 1 ml of the solution is removed, 1 ml of a solution of Br$_2$ in CCl$_4$ is added and GC analysis is effected.

0.51/22.4 (l/mol)=0.0223 moles of ethylene used up
Activity: 250.5 moles of ethylene/V moles
Selectivity: 56% to 1-hexene

EXAMPLE 5

81 mg of V(mes)$_2$(OCOCF$_3$) (MW=404; 2·10$^{-4}$ mmoles) are charged under argon into a 250 ml three-necked flask. 30 ml of anhydrous and degassed toluene are added. The brown solution under ethylene becomes lighter. After 10 minutes an absorption equal to 67 ml of ethylene is obtained. After 1 hour, as there no longer seems to be any more absorption, 0.080 ml of 2,5-dimethyl-pyrrole (0.787 mmoles) are added, which causes a further ethylene absorption equal to 33 ml. The green solution, after a night at room temperature, becomes brown again and is analyzed via GC.

0.11/22.4 (l/mol)=0.00446 moles of ethylene used up
Activity: 22.26 moles of ethylene/vanadium mole
Selectivity: 55% to 1-hexene

EXAMPLE 6

56 mg of V(mes)$_2$(OCOCF$_3$) (MW=404; 0.138 mmoles) are charged under argon into a 100 ml three-necked flask. 0.042 ml of 2,5-dimethylpyrrole (0.408 mmoles) are added to 20 ml of distilled and degassed cyclohexane. The orange solution under ethylene darkens. It is left at 50° C. for 5 hours; after 3 hours the solution is green and has absorbed 70 ml of ethylene. GC analysis is effected.

0.071/22.4 (l/mol)=0.003125 moles of ethylene used up
Activity: 22.54 moles of ethylene/vanadium mole
Selectivity: 46% to 1-hexene

EXAMPLE 7

64 mg of V(mes)$_2$B(Ph)$_4$ (MW=610; 1.04·10$^{-4}$ moles) are charged under argon into a 100 ml three-necked flask. The mixture is dispersed in 30 ml of anhydrous toluene. The reddish-brown suspension under ethylene darkens. It is left at room temperature for 20 hours. After this period of time a black suspension is formed. In 10 minutes, 70 ml of ethylene are absorbed. It is injected into GC.

0.071/22.4 (l/mol) 0.00315 moles of ethylene used up
Activity: 29.8 moles of ethylene/vanadium mole
Selectivity: 66% to 1-hexene

EXAMPLE 8

0.2 ml of V(mes)$_2$ at 6% in hexane (MW=291; 4.12·10$^{-5}$ moles) in 20 ml of degassed and anhydrous toluene are charged under argon into a 100 ml test-tube. 21 mg of $Cp_2Fe(BPh_4)$ (MW=505; $4.12 \cdot 10^{-5}$ moles) are added to the orange solution. The orange solution is diluted up to 100 ml with toluene, charged into a Buchi 300 ml glass autoclave and is put under 7 bars of ethylene and maintained at room temperature for 1 hour. It is observed that as ethylene is absorbed, the solution becomes turbid. The autoclave is degassed and the contents discharged without diluting. 1 ml of the solution is removed, 1 ml of a solution of $Br_2$ in $CCl_4$ is added and injected into GC: only 1-hexene is present.

Activity: 605 moles of ethylene/V mole

Selectivity: 99% to 1-hexene

EXAMPLE 9

30 mg of $V(mes)_2I$ (MW=418; $7.17 \cdot 10^{-5}$ moles) in 100 ml of degassed and anhydrous toluene are charged under argon into a 100 ml test-tube. The orange solution is charged into a Buchi 300 ml glass autoclave, put under 7 bars of ethylene and maintained at room temperature for 1 hour. The autoclave is degassed and the contents discharged without diluting. 1 ml of the solution is removed, 1 ml of a solution of $Br_2$ in $CCl_4$ is added and injected into GC: no olefins are present.

Activity: 0 moles of ethylene/v mole

Selectivity: 0% to 1-hexene

| | Catalytic precursor (mmoles) | Solvent (ml) | P (bar) | Activity (ethylene moles)/ (V mole) | Selectivity (mole %) |
|---|---|---|---|---|---|
| | OLIGOMERIZATION TESTS OF ETHYLENE CATALYZED BY V(I) | | | | |
| 4 | $V(mes)_2(OCOCF_3)$ (0.089) | Toluene (20) | 1 | 250.5 | 56 |
| 5 | $V(mes)_2(OCOCF_3)$ + 2,5-dimethyl pyrrole (0.2) | Toluene (30) | 1 | 22.26 | 55 |
| 6 | $V(mes)_2(OCOCF_3)$ + 2,5-dimethyl pyrrole (0.138) | Cyclohexane (25) | 1 | 22.54 | 46 |
| 7 | $V(mes)_2(BPh_4)$ (0.1) | Toluene (30) | 1 | 29.8 | 66 |
| 8 | $V(mes)_2$ 6% + $Cp_2Fe(BPh_4)$ ($4.12 \cdot 10^{-5}$ moles) | Toluene (100) | 7 | 605 | 99 |
| 9 | $V(mes)_2I$ ($7.17 \cdot 10^{-5}$ moles) | Toluene (100) | 7 | 0 | 0 |

Tests carried out at room temperature for 1 hour.

What is claimed is:

1. A process for the preparation of 1-hexene comprising oligomerizing ethylene in the presence of a catalyst wherein said catalyst comprises a vanadium complex having the formula:

$(arene)_2VX$ wherein the term arene represents benzene or mono-, di-, or tri-alkylsubstituted benzene, V is a vanadium ion with a low oxidation state, and X is an anion selected from the group consisting of a non-coordinating anion, a carboxylate, and a sulphonate.

2. The process as claimed in claim 1, wherein the vanadium complex is selected from the group consisting of bis-(mesitylene)-vanadium trifluoroacetate, bis-(mesitylene)-vanadium-tetraphenylborate and bis-(mesitylene)-vanadium-tetrachloroaluminate.

3. The process as claimed in claim 1, wherein said catalyst further comprises a hetero-cyclic compound.

4. The process as claimed in claim 3, wherein the heterocyclic compound is selected from the group consisting of pyrroles, substituted pyrroles, phenanthroline and pyridine.

5. The process as claimed in claim 3, wherein a molar ratio between the heterocyclic compound and the vanadium complex ranges from 1 to 20.

6. The process as claimed in claim 1, wherein the ethylene is oligomerized in the presence of a solvent selected from the group consisting of aromatic hydrocarbons and aliphatic hydrocarbons.

7. The process as claimed in claim 6, wherein the solvent is toluene or cyclohexane.

8. The process as claimed in claim 1, wherein the ethylene is oligomerized at a temperature less than or equal to 150° C.

9. The process as claimed in claim 8, wherein the ethylene is oligomerized at a temperature ranging from 25 to 60° C.

10. The process as claimed in claim 1, wherein the ethylene is oligomerized at a pressure ranging from 1 to 100 atmospheres.

11. The process as claimed in claim 10, wherein the ethylene is oligomerized at a pressure ranging from 1 to 50 atmospheres.

12. The process as claimed in claim 1, wherein the ethylene is oligomerized for less than 36 hours.

13. The process as claimed in claim 12, wherein the ethylene is oligomerized for from 1 to 24 hours.

14. The process as claimed in claim 1, wherein the non-coordinating anion is selected from the group consisting of $B(Ar)_4^-$ and $AlCl_4^-$.

* * * * *

UNITED STATES PATENT AND TRADEMARK OFFICE
CERTIFICATE OF CORRECTION

PATENT NO. : 6,459,007 B1 Page 1 of 1
DATED : October 1, 2002
INVENTOR(S) : Santi et al.

It is certified that error appears in the above-identified patent and that said Letters Patent is hereby corrected as shown below:

<u>Title page,</u>
Item [75], inventors, should read -- [75] Inventors: Roberto Santi; Anna Maria Romano, both of Novara; Manuela Grande, Vercelli; Anna Sommazzi, Genova; Francesco Masi, Lodi; Antonio Proto, Novara, all of (IT) --
Item [30], the Foreign Application Priority Data should read:
-- [30]       Foreign Application Priority Data
Mar. 17, 2000   (IT) ........................................ MI2000A0546 --

Signed and Sealed this

Twenty-first Day of January, 2003

JAMES E. ROGAN
*Director of the United States Patent and Trademark Office*